United States Patent [19]

Heminway et al.

[11] Patent Number: 4,893,991

[45] Date of Patent: Jan. 16, 1990

[54] METHOD AND MEANS FOR IMPROVING EFFICIENCY OF PERISTALTIC PUMPS

[76] Inventors: James F. Heminway, 10899 W. Shelby, Medina, N.Y. 14103; Eric P. Freischlag, 4281 Chestnut Rd., Wilson, N.Y. 14172

[21] Appl. No.: 262,205

[22] Filed: Oct. 19, 1988

Related U.S. Application Data

[63] Continuation of Ser. No. 55,982, May 27, 1987, abandoned.

[51] Int. Cl.[4] .......................... F04B 43/12; F04B 45/08
[52] U.S. Cl. ......................................... 417/53; 417/474
[58] Field of Search .......................... 417/53, 474, 477; 604/153

[56] References Cited

U.S. PATENT DOCUMENTS

| | | | |
|---|---|---|---|
| 4,138,205 | 2/1979 | Wallach | 417/477 X |
| 4,155,362 | 5/1979 | Jess | 417/477 X |
| 4,479,797 | 10/1984 | Kobayashi et al. | 417/474 X |
| 4,482,347 | 11/1984 | Borsanyi | 417/474 X |
| 4,671,792 | 6/1987 | Borsanyi | 417/474 X |

FOREIGN PATENT DOCUMENTS 56-113088 9/1981 Japan ..................... 417/477

Primary Examiner—Carlton R. Croyle
Assistant Examiner—Eugene L. Szczecina, Jr.
Attorney, Agent, or Firm—McDermott, Will & Emery

[57] ABSTRACT

The efficiency and accuracy of a peristaltic pump is increased simply and inexpensively by controlling the cross sectional configuration of the section of flexible tubing which is operated upon the pump thrust members during a pumping operation. Specifically, the section of tubing, which is normally generally cylindrical in configuration, is held partially constricted or compressed upon being mounted in the pump, so that it becomes generally oval in cross sectional configuration. The thrust members of the pump, when the latter is operating, thus repeatedly compress a section of tubing which is already partially compressed, and which never is allowed to expand fully back to its cylindrical configuration. This substantially reduces the drop in feed rate heretofore experienced by similar pumps because of tubing fatigue and augment.

9 Claims, 1 Drawing Sheet

METHOD AND MEANS FOR IMPROVING EFFICIENCY OF PERISTALTIC PUMPS

This application is a continuation of U.S. application Ser. No. 07/055,982, filed May 27, 1987, now abandoned.

BACKGROUND OF THE INVENTION

This invention relates to peristaltic pumps, and more particularly to a novel method and means for increasing the pumping accuracy of such pumps, and even more particularly to peristaltic pumps of the linear variety.

Peristaltic pumps of the type described are particularly suited for use in accurately metering and infusing fluids into the bodies of hospital patients, and the like. The U.S. Pat. Nos. 4,217,933, 4,346,705, 4,299,218, and 4,210,138 disclose one type of fluid infusion and metering equipment which is commonly used today in hospitals and other such institutions where extreme accuracy in the infusion of fluids is very important. This system uses a rotary or roller-type peristaltic pump, as disclosed for example in U.S. Pat. Nos. 4,155,362 and 4,210,138.

One major disadvantage of a system of the type noted above is that it is extremely complicated and expensive. The reason for this is that the peristaltic pump, which is the essence of the equipment, operates in the usual manner repeatedly to compress and expand a section of resilient tubing through which the metered fluid is pumped. This tubing typically is made from a flexible, plastic material such as polyvinyl chloride or the like. As is well known to those skilled in the art, the section of the tubing which passes through the peristaltic pump is intermittently compressed and released at spaced points along its length. It is this alternate expansion and contraction of the tubing, which effects the pumping of the fluid. This is true whether the pump is of the rotary type described above, or of the linear variety, such as shown for example in FIG. 4 of the U.S. Pat. No. 4,155,362.

Regardless of the particular type of peristaltic pump employed, its Achilles' heel is the need for utilizing the flexible tubing, the characteristics of which are subject to change in response to ambient temperature variations, fatigue during prolonged use, tubing eccentricity, etc. Motor speed, the speed of the peristaltic rotor or drive shaft is also a source of error during metering, but this factor (the speed of the rotor) can be controlled very accurately by available, inexpensive control devices. However, the variables in the fluid feed rate that are introduced by virtue of the presence of the plastic tubing have been far more difficult to control.

For example, because of fatigue, tubing elasticity and hence its inner diameter can vary rather drastically during use, and as a consequence the metering rate and pumping efficiency will vary accordingly. In practice, many conventional metering systems of the type described have been found to exhibit as much as a 10% drop in flow rate in a twenty-four hour period. By using rather sophisticated control systems of the type disclosed in the above-noted U.S. patents, it has been possible to reduce this drop to as much as 6 to 7%. However, for many infusion systems even this rather limited drop in the flow rate is undesirable if not intolerable.

It is an object of this invention, therefore, to provide a novel method of stabilizing the pumping rates of peristaltic pumps without requiring the use of any particular types of tubing with the pumps.

Another object is to provide improved metering apparatus of the type described which is capable of substantially reducing the undesirable drop in the flow rate of the apparatus heretofore encountered during prolonged use.

It is a further object of this invention to provide improved metering apparatus of the type described which utilizes relatively simple and inexpensive means for substantially increasing the pumping accuracy of the apparatus.

Still another object of this invention is to provide for fluid infusion systems or equipment of the type described improved peristaltic pump means which is capable of increased pumping efficiency even when employing standard, flexible tubing, rather than utilizing any special type of tubing.

Still other objects of the invention will be apparent hereinafter from the specification and from the recital of the appended claims, particularly when read in conjunction with the accompanying drawings.

SUMMARY OF THE INVENTION

The pump employed with the illustrated metering apparatus is a linear peristaltic pump having a plurality of reciprocable pushers or fingers driven at one end by a like plurality of annular cams that are carried by a drive shaft, and engagable at their opposite or operating ends with a section of plastic tubing through which fluid is to be pumped. The section of the tubing is releasably held over or against the operating ends of the fingers by a flat backup plate, which is carried by a door that is mounted on a housing to be swung into a closed position in which it releasably secures the backup plate against the side of the tubing section remote from the fingers.

Normally in prior art devices the fingers, or in the case of a rotary peristaltic pump the associated rollers, repeatedly cause the registering section of tubing to be compressed and expanded during a pumping operation. Each expansion step permits the tubing to return to its normal, cylindrical configuration. The present invention involves designing the pump so that the flexible tubular section which is subjected to compression and expansion is never allowed, from the outset, to assume a truly cylindrical configuration. Instead, the operating cams are designed to maintain the tubular section oval in cross section. This has been found to be effective in considerably reducing the drop in flow rate previously experienced by known metering systems.

THE DRAWINGS

DETAILED DESCRIPTION OF THE PREFERRED EMBODIMENTS

Figure 1:
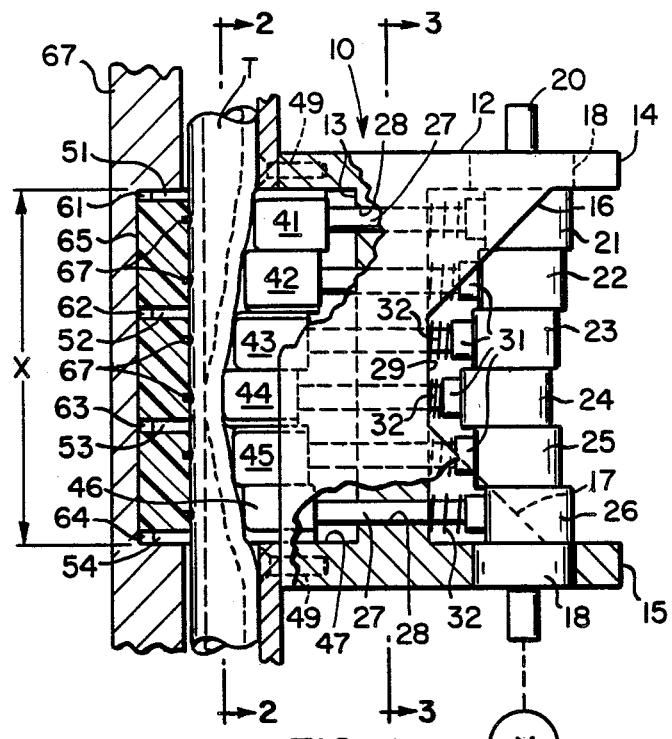
FIG. 1 is a fragmentary side elevational view of part of fluid infusion and metering apparatus having an improved peristaltic pump made according to one embodiment of this invention, portions of the apparatus being cut away and shown in section.

Referring now to the drawings by numerals of reference and first to FIGS. 1 to 3, 10 denotes generally a linear peristaltic pump mechanism which forms part of a fluid infusion or metering system of the type described above. The pumping mechanism 10 comprises a stationary pump body 12, which is secured in a conventional metering housing (not illustrated), such as for example a housing of the type which forms part of the volumetric infusion pump, that is sold by the Assignee of the present invention under the trademark "SIGMA 6000". The body 12, which is generally rectangular in cross section, has in its forward or left end (FIG. 2) a large, rectangular recess 13 that is used for a purpose noted hereinafter. Integral with and projecting rearwardly from the solid central section of the pump body 12 are two, vertically spaced, parallel wings or projections 14 and 15, the marginal side edges of which are connected to the central section of body 12 by two sets of inclined web section 16 and 17, respectively.

Rotatably secured adjacent opposite ends thereof in a pair of annular bearings 18, which are secured in registering openings in projections 14 and 15, is a cam drive shaft 20. Secured to shaft 20 for rotation thereby eccentrically about its axis between the projections 14 and 15 are six annular cams, which in FIG. 1 are denoted by the numerals 21 through 26. These cams register with six, identical operating rods 27, which are mounted to reciprocate intermediate their ends in six spaced, parallel bores 28, which are formed in the central section of body 12. Each bore 28 opens at one end on the bottom of the recess 13 and at its opposite end on a plane, transverse surface 29, which is formed on the rear or right end (FIG. 1) of the central section of the body 12 to extend vertically between the projections 14 and 15 in spaced, confronting relation to the cams 21 through 26.

Each rod 27 has secured on its rear or right end, as shown in FIG. 1, an enlarged-diameter cap 31, which is slidably engaged at its outer end with the peripheral surface of one of the cams 21 through 26, and at its inner end with a compression spring 32, which surrounds each rod 27 between the surface 29 and the associated cap 31. Each spring 32 thus resiliently urges the associated rod 27 toward the right in FIG. 1 relative to body 12, thereby resiliently to retain the associated cap 31 in sliding engagement with the outer peripheral surface of one of the cams 21 through 26.

Secured to the opposite or left end (FIG. 1) of each rod 27 for reciprocation thereby in the recess 13 is one of six, rectangularly shaped, tube-engaging fingers or pushers, which are denoted by the numerals 41 through 46 in FIG. 1. These fingers project through a large rectangular slot or opening 47, which is formed in a cover plate 48 that is secured over the left or outer end of the body 12 by a plurality of screws 49 so that its opening 47 registers with the rectangular recess 13 in body 12.

Figure 2:
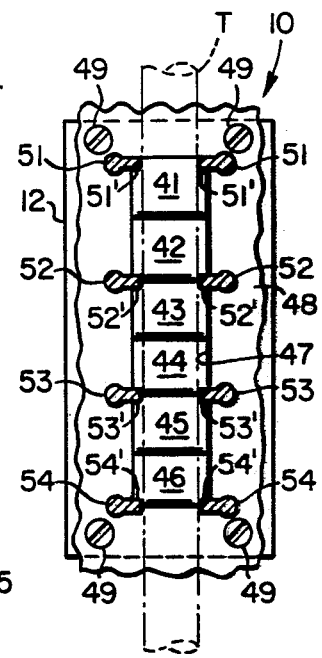
FIG. 2 is a fragmentary sectional view taken generally along the line 2—2 in FIG. 1 looking in the direction of the arrows.
Figure 3:
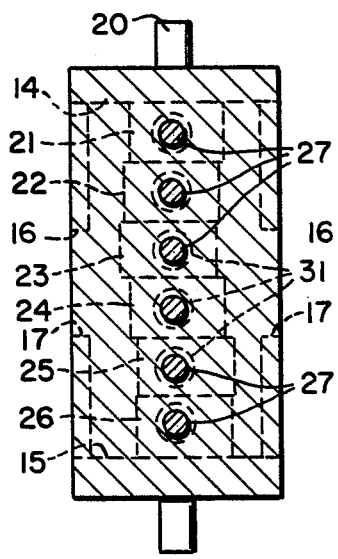
FIG. 3 is a fragmentary sectional view taken generally along the line 3—3 in FIG. 1 looking in the direction of the arrows.

Secured to plate 48 adjacent the edge of its opening 47, and projecting outwardly from the plate (toward the left as shown in FIG. 1) are four, vertically spaced pairs of combination tube/finger guides denoted at 51, 52, 53 and 54, respectively. As shown more clearly in FIG. 2, the two guides of each pair 51 through 54 are located at opposite sides, respectively of slot 47, and have narrow rib sections 51' through 54', respectively, which are disposed to project slidably into corresponding notches formed in the opposed side edges of at least certain of the fingers 41 through 46. Specifically, the ribs 51' as shown in FIG. 2, project into registering recesses formed in the upper side edges of the finger 41; the ribs 52' project into registering recesses formed in the opposed side edges of the confronting surfaces on fingers 42 and 43; the ribs 53' project into registering recesses formed in opposite sides of the confronting surfaces of fingers 44 and 45; and the ribs 54' project into registering recesses formed in opposite sides of the bottom surface of finger 46. The projections 51 through 54 thus serve slidably to guide the fingers 41 through 46 for reciprocation in predetermined paths upon the rotation of shaft 20, as noted hereinafter.

As shown in FIG. 1, the projections 51 through 54 (only one of each pair of which is shown in FIG. 1) project into registering recesses 61 through 64, respectively, which are formed in a rectangularly shaped, plastic backup plate 65. Plate 65 is mounted on a hinged cover or door 67, which forms part of the above-noted housing for the "SIGMA 6000" pump apparatus, and which is disposed to be swung into and out of an operative position in which it secures the plate 65 releasably in the position as shown in FIG. 1. (Although only one projection 51 through 54 of each pair thereof, and the corresponding registering recesses 61 through 64 are shown in FIG. 1, it will be understood that like recesses 61 through 64 are formed in the plate 65 to accommodate the remaining projections 51 through 54 that extend from plate 48.)

In use, a flexible tube T, through which fluid is to be pumped, is positioned intermediate its ends across the face of the cover plate 48 so that the tube extends (as shown by broken lines in FIG. 2) vertically between the pairs of projections 51 through 54 on plate 47, and in overlying relation to the outer ends of the pushers or fingers 41 through 46. The door 67 is then swung closed, or into the position as shown in FIG. 1, so that the projections 51 through 54 enter the registering recesses 61 through 64 in plate 65, thus allowing plate 65 to engage the registering section of the tube T at the side thereof remote from the fingers 41 through 46. At this time the side of the tube T remote from the cover plate 48 is also engaged by each of six, narrow metal strips 67, which are embedded in and project slightly from the face of plate 65 along transverse lines that register substantially with the midpoints of the opposed fingers 41 through 46, respectively. These strips 67, which are conventional, cooperate with the fingers 41 through 46 during operation of the latter to effect the desired restriction of the tube T.

After the door 67 has been releasably secured in its closed position, the cam shaft 20 is rotated by a motor M which is carefully controlled by a mechanism that forms no part of this invention. As shaft 20 rotates its cams 21 through 26 effect the desired reciprocation of the rods 27 and the pushers 41 through 46 attached thereto. As will be apparent to one skilled in the art, the fingers 41 through 46 are repeatedly extended by the cams 21 through 26 and retracted by springs 32 in order repeatedly and progressively to compress and then release the tubing T in the section thereof denoted at X in FIG. 1, thereby causing fluid in the tube to be pumped unidirectionally through the tube in a known manner. Although this mode of operating a linear peristaltic pump is, generally speaking, well known to the prior art, the pump disclosed herein is unique in that the cams 21 through 26 are designed to manipulate the pushers 41 through 46 in a manner heretofore unknown and unappreciated by the prior art.

Figure 4:
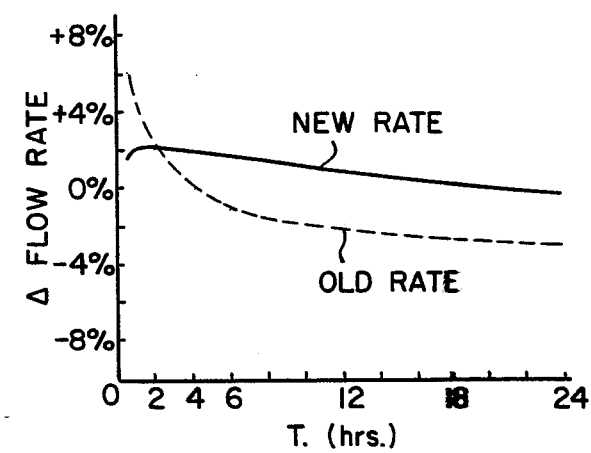
FIG. 4 is a graphical representation of the new rate of change of the flow rate of this improved metering apparatus, as compared to the rate of change of the flow rate of known such apparatus.

For example, as noted above, one of the major problems encountered during the use of flexible tubing in combination with known peristaltic pumps is that the flow rate or output of the pump tends to vary rather considerably during use, and as shown for example in FIG. 4, this variation is greatest during the initial operation of the pump. Tubing durometer and the concentricity of the inner and outer diameters of the tubing are directly responsible for the drop in flow rate accuracy over a period of time. As that portion of the tubing which is located in the pumping section (the portion denoted by X in FIG. 1) is subjected again and again to the pressure of being pinched off or compressed by the pump fingers 41 through 46, it fatigues and loses some of its ability to open back up. Also, if the tubing is nonconcentric its "effective" area may change dramatically for some orientations of the tubing in the pumping section of the pump. As a consequence, this results in a drop in the flow rate delivery over a period of time; and the harder and more eccentric the tubing the more pronounced is the drop. Moreover, as shown graphically in FIG. 4, most of the deformation of the tubing takes place within the first six hours of operating time, and for this reason it is customary normally to design the unit so that it pumps at the outset at a rate slightly greater than the desired rate to compensate for the loss in flow rate which normally occurs as the equipment is utilized over a prolonged period of time.

For example, in FIG. 4 the broken line denotes graphically the percentage in change of the flow rate which occurs in a conventional metering system utilizing known peristaltic pumps. The solid line graph, on the other hand, represents the rate of change which occurs in the flow rate when utilizing applicants' improved pumping mechanism. It will be noted that whereas the percentage of change of the flow rate (old rate) for known metering apparatus ranges from a −6% to approximately a −3%, it has been possible utilizing applicants' equipment to reduce this percentage of change in the rate to the very low range of approximately +2% to approximately 0% change. This significant improvement has been achieved by substantially eliminating or minimizing the very rapid drop in flow rate that heretofore tended to occur during the initial six hours of operation of the equipment.

This improvement has been effected by the above-described equipment by designing the cams 21 through 26 so that when the tube T is inserted in the equipment and the door 67 is closed, the entire section of the tubing T engaged by the pushers 41 through 46—i.e., the section denoted by the letter X in FIG. 1—will be at least partially compressed, so that although the bore in the tube T normally would be circular in cross section, at least for the section X of the tubing its bore will be oval in cross sectional configuration. For example, referring to FIG. 1, finger 46 is shown in its approximately fully retracted position, while finger 44 is shown to be in its approximately fully advanced position, wherein finger 44 has, in essence, compressed the tubing T to a point in which its bore is completely closed in that region which registers with pusher 44. Pusher 46, on the other hand, which is typical of the extreme right hand position which each pusher 41 through 46 is capable of assuming, has not been retracted far enougph to permit the tubing T completely to resume its normal, cylindrical configuration. Therefore, as the cams 21 through 26 reciprocate the pushers 41 through 46, the section X of the tubing T will never be allowed at any point therealong to return to its fully, cylindrical configuration.

The result is that the pump mechanism 10 eliminates the need for the tube fully to reopen or resume its cylindrical configuration each time the adjacent finger is withdrawn to a retracted position. By eliminating the need for the tubing to return to its cylindrical configuration after each compression stage thereof applicants' apparatus eliminates the loss in the flow rate which is inherent during the early stages of operation (for example the first six hours) of known peristaltic metering equipment, that is, equipment of the type in which the pump rollers or fingers permit the tubing fully to reopen to its cylindrical configuration after each compression thereof. Since it is possible easily to maintain the speed of rotation of the cam drive shaft 20 to within + or −0.1%, it will be apparent that applicants' invention considerably improves the overall efficiency of operation of peristaltic pumping mechanisms of the type described above, as compared to prior such mechanisms. It will also be apparent, that in connection with the illustrated embodiment, this improvement has been achieved very inexpensively, simply by reducing the throw of the associated cams that drive the tube compressing fingers 41 through 46, and without the need for utilizing complicated or expensive electronic control circuitry. Moreover, it would be applicable to any type of peristaltic pump in which one or more compression members operate to induce fluid flow along a flexible section of tubing by repeatedly contracting the section at a point and cyclically moving the contraction along the tubing section to force fluid along the tube in front of the restriction without permitting any portion of the tubing section to return to its noraml, cylindrical confiuration.

From the foregoing, it will be apparent that the present invention provides relatively simple and inexpensive means for considerably increasing the efficiency of peristaltic pumping mechanisms while utilizing conventional, flexible tubing of the type which is readily available in the marketplace, and does not require any special tubing. Moreover, although this invention has been illustrated and described in detail in connection with only one embodiment thereof, it will be apparent that it is capable of still further modification, and that this application is intended to cover any such modifications as may fall within the scope of one skilled in the art or the appended claims.

We claim:

1. A method of improving the efficiency of peristaltic pumps of the type which utilize a plurality of reciprocable fingers for repeatedly contracting a section of flexible tubing at a point, and moving the point of contraction unidirectionally and cyclically along the tube section to force fluid along the tube section in front of the contraction, comprising mounting a section of flexible, generally cylindrical tubing having a bore in a peristaltic pump, said section being in operative relation to said fingers, partially constricting said tubular section so that each portion of said tubular section is compressed along its length, and causing said fingers repeatedly to compress and release said partially constricted tubular section by cyclically urging said fingers successively and one after the other into extended positions in which each finger substantially closes the bore at a point along said tubular section and retracted positions in which each member is drawn away from said tubular section but only far enough to permit said tubular section to assume a generally oval configuration in cross section without permitting any portion of said section to return to its generally cylindrical configuration, whereby the drop in the flow rate of said pump, during operation thereof, is maintained in a range of approximately +2% to 0% by preventing any portion of said section from returning to its generally cylindrical configuration during reciprocation of said fingers.

2. A method as defined in claim 1, in which said fingers constrict said tubular section to varying degrees along its axial length between a maximum value in which the bore in said tubular section is closed at said point of contraction, and a minimum value in which said bore is oval in cross sectional configuration along the remaining axial length of said section.

3. The method of improving the efficiency of peristaltic pumps recited in claim 1, in which said fingers are disposed in side-by-side relation immediately adjacent each other.

4. The method of improving the efficiency of peristaltic pumps recited in claim 2, in which said fingers are disposed in side-by-side relation immediately adjacent each other.

5. Fluid pumping and metering apparatus, comprising
a peristaltic pump housing having an opening in one end thereof,
means for removably mounting across said opening a section of flexible tubing which normally is generally cylindrical in cross section,
means for compressing said section at each point along its length when said section is mounted across said opening,
pump means in said housing including a rotatable drive shaft and having a plurality of cams mounted thereon, said pump means further including a plurality of reciprocable fingers mounted in said housing for engagement at one end with said cams and at their opposite ends through said opening with said tubular section at spaced points therealong,
means for rotating said shaft thereby to effect reciprocation of said fingers, and thereby cyclically to urge said fingers successively and one after the other into extended positions in which each member closes the bore in the registering portion of said tubular section, and retracted positions in which each member is drawn away from the tubular section but only far enough to permit the registering portion of said tubular section to assume a generally oval configuration in cross section, whereby during a pumping operation the drop in the flow rate of said pump is maintained in a range of approximately +2% to 0% by preventing any portion of said section from assuming a cylindrical configuration along any portion of its length.

6. The fluid pumping and metering apparatus of claim 5, in which said fingers are mounted in said housing in side-by-side relation immediately adjacent each other.

7. The fluid pumping and metering apparatus of claim 5, in which said mounting means further includes guide means cooperating with said fingers for causing said fingers to reciprocate in predetermined paths upon the rotation of said shaft.

8. The fluid pumping and metering apparatus of claim 7, in which said guide means maintains said fingers in side-by-side relation immediately adjacent each other during rotation of said shaft.

9. Fluid pumping and metering apparatus as defined in claim 5, wherein
said mounting means comprises a cover member mounted on said housing for movement into and out of a closed position in which it is releasably secured over said opening with said tubular section of said tubing extending transversely across said opening between said cover member and said housing, and
said cams having operating surfaces movable toward and away from said cover member, and operable to cause the cross sectional area of the bore in said tubular section repeatedly to be constricted progressively from said partially constricted oval configuration to a substantially fully constricted configuration, and unidirectionally from one end to the other of said tubular section.

* * * * *